United States Patent

Draber et al.

[11] Patent Number: 4,846,876
[45] Date of Patent: Jul. 11, 1989

[54] HERBICIDAL IMIDAZO-PYRROLO-PYRIDINE DERIVATIVES

[75] Inventors: Wilfried Draber, Wuppertal; Hans-Joachim Santel, Leverkusen; Robert R. Schmidt, Bergisch Gladbach; Robert H. Strang, Duesseldorf, all of Fed. Rep. of Germany

[73] Assignee: Bayer Aktiengesellschaft, Leverkusen, Fed. Rep. of Germany

[21] Appl. No.: 101,621

[22] Filed: Sep. 28, 1987

[30] Foreign Application Priority Data

Oct. 14, 1986 [DE] Fed. Rep. of Germany ....... 3634952

[51] Int. Cl.$^4$ .................... A01N 43/50; C07D 471/14
[52] U.S. Cl. ........................................ 71/92; 546/15; 546/23; 546/82
[58] Field of Search .................. 546/82, 15, 23; 71/92

[56] References Cited

U.S. PATENT DOCUMENTS

4,717,414  1/1988  Hunt .................................. 546/82 X

FOREIGN PATENT DOCUMENTS

0195745  9/1986  European Pat. Off. ................ 71/92

*Primary Examiner*—Richard A. Schwartz
*Attorney, Agent, or Firm*—Sprung Horn Kramer & Woods

[57] ABSTRACT

An imidazo-pyrrolo-pyridine compound of the formula (I),

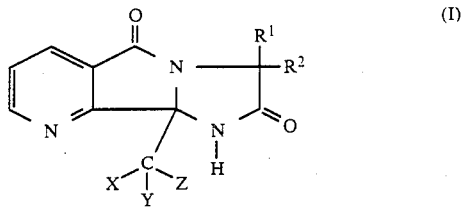

in which
  $R^1$ and $R^2$, independently of one another, represent alkyl, or together represent a doubly linked alkylene radical,
  x represents hydrogen, halogen or alkyl,
  y represents hydrogen, halogen, cyano, alkyl, optionally substituted aryl, alkylsulphonyl, dialkoxyphosphoryl or a

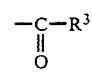

radical, and
z represents cyano, nitro or a

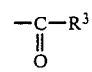

radical,
where
  $R^3$ represents alkyl, alkoxy, cycloalkyl, amino or alkoxycarbonyl. The compound is useful as a herbicide.

6 Claims, No Drawings

HERBICIDAL IMIDAZO-PYRROLO-PYRIDINE DERIVATIVES

The invention relates to new imidazo-pyrrolo-pyridine derivatives, a process for their preparation, and their use as herbicides.

It has already been disclosed that certain 2-(2-imidazolin-2-yl)-pyridines, such as, for example, 2-(4,4-dimethyl-5-oxo-2-imidazolin-2-yl)-3-methoxycarbonyl-pyridine, have herbicidal properties (cf., for example, EP-OS (European Published Specification) 41,623).

However, the herbicidal action of these previously known compounds against weeds is not always completely satisfactory in all areas of application.

New imidazo-pyrrolo-pyridine derivatives of the general formula (I),

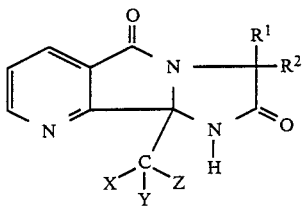 (I)

in which
R$^1$ and R$^2$, independently of one another, represent alkyl, or together represent a doubly linked alkylene radical,
X represents hydrogen, halogen or alkyl,
Y represents hydrogen, halogen, cyano, alkyl, optionally substituted aryl, alkylsulphonyl, dialkoxyphosphoryl or a

radical, and
Z represents cyano, nitro or a

radical,
where
R$^3$ represents alkyl, alkoxy, cycloalkyl, amino or alkoxycarbonyl,
have been found.

It has furthermore been found that the new imidazo-pyrrolo-pyridine derivatives of the formula (I),

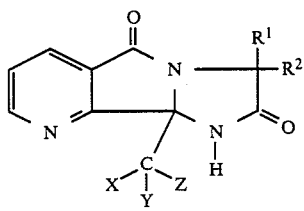 (I)

in which

R$^1$ and R$^2$, independently of one another, represent alkyl, or together represent a doubly linked alkylene radical,
X represents hydrogen, halogen or alkyl,
Y represents hydrogen, halogen, cyano, alkyl, optionally substituted aryl, alkylsulphonyl, dialkoxyphosphoryl or a

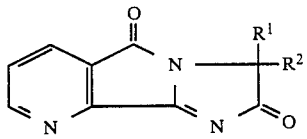

radical, and
Z represents cyano, nitro or a

radical,
where
R$^3$ represents alkyl, alkoxy, cycloalkyl, amino or alkoxycarbonyl,
are obtained when imidazo-pyrrolo-pyridines of the formula (II),

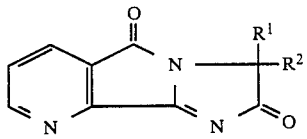 (II)

in which
R$^1$ and R$^2$ have the abovementioned meanings, are reacted with substituted methane derivatives of the formula (III),

 (III)

in which
X, Y and Z have the abovementioned meaning,
in the presence of a basic reaction auxiliary and if appropriate in the presence of a diluent.

Finally, it has been found that the new imidazo-pyrrolo-pyridine derivatives of the formula (I) have herbicidal properties.

Surprisingly, the imidazo-pyrrolo-pyridine derivatives of the formula (I) according to the invention have a considerably greater herbicidal potency than the 2-(2-imidazolin-2-yl)-pyridines which are known from the state of the art, such as, for example, 2-(4,4-dimethyl-5-oxo-2-imidazolin-2-yl)-3-methoxycarbonyl-pyridine, which are similar compounds chemically and regarding their action.

Formula (I) provides a general definition of the imidazo-pyrrolo-pyridine derivatives according to the invention. Preferred compounds of the formula (I) are those in which
R$^1$ and R$^2$, independently of one another, represent straight-chain or branched alkyl having 1 to 8 carbon atoms, or together represent a doubly linked straight-chain or branched alkylene radical having 3 to 10 carbon atoms, X represents hydrogen, fluorine, chlorine, bromine or iodine, or straight-chain or branched alkyl having 1 to 8 carbon atoms, Y represents hydrogen, fluorine, chlorine, bromine, iodine, cyano, straight-chain or branched alkyl having 1 to 8 carbon atoms or phenyl which is optionally monosubstituted or polysubstituted, the substituents being identical or different and suitable substituents being: halogen, cyano, nitro and in each case straight-chain or branched alkyl or halogenoalkyl in each case having 1 to 4 carbon atoms and, in the case of halogenoalkyl, having 1 to 9 identical or different halogen atoms; in addition represents alkylsulphonyl having 1 to 4 carbon atoms in the alkyl part or dialkoxyphosphoryl having 1 to 4 carbon atoms in each of the individual alkoxy parts, or a radical, and

Z represents cyano, nitro or a

radical,
where
R³ represents in each case straight-chain or branched alkyl, alkoxy or alkoxycarbonyl in each case having 1 to 6 carbon atoms cycloalkyl having 3 to 7 carbon atoms or amino. Particularly preferred compounds of the formula (I) are those in which R¹ and R², independently of one another, represent methyl, ethyl, n- or i-propyl and n-, i-, s- or t-butyl, or together represent a 1,3-propanediyl radical, a 1,4-butanediyl radical or a 1,5-pentanediyl radical which is in each case doubly linked, X represents hydrogen, fluorine, chlorine, bromine, methyl, ethyl, n- or i-propyl, n-, i-, s- or t-butyl, Y represents hydrogen, fluorine, chlorine, bromine, cyano, methyl, ethyl, n- or i-propyl, n-, i-, s- or t-butyl, or phenyl which is optionally monosubstituted, disubstituted or trisubstituted, the substituents being identical or different and suitable substituents being: fluorine, chlorine, bromine, cyano, nitro, methyl, ethyl or trifluoromethyl; in addition represents methylsulphonyl, ethylsulphonyl, dimethoxyphosphoryl, diethoxyphosphoryl or a

radical,
Z represents cyano, nitro or a

radical,
where
R³ represents methyl, ethyl, n- or i-propyl, n-, i-, s- or t-butyl, methoxy, ethoxy, n- or i-propoxy, methoxycarbonyl, ethoxycarbonyl, cyclopropyl, cyclohexyl or amino.

The compounds of general formula (I) listed in the preparation examples may be mentioned individually as specifically preferred.

If, for example, 3-isopropyl-3-methyl-5H-imidazo[1',2':1,2]-pyrrolo-[3,4-b]-pyridine-2-(3H),5-dione and methyl cyanoacetate are used as starting materials, then the course of the reaction of the process according to the invention may be represented by the following equation:

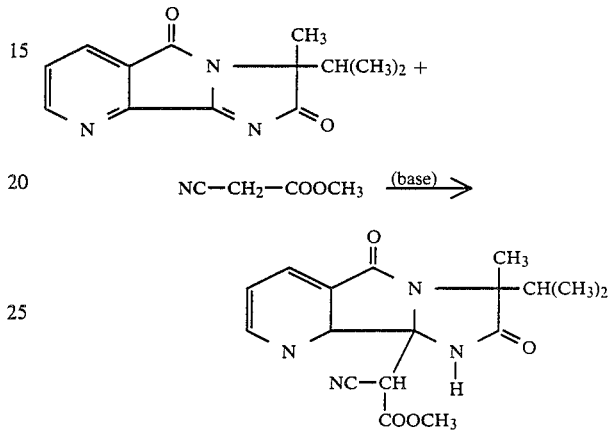

Formula (II) provides a general definition of the imidazo-pyrrolopyridines required as starting materials for carrying out the process according to the invention. In this formula (II), R¹ and R² preferably represent those radicals which have already been mentioned in connection with the description of the substances of the formula (I) according to the invention as being preferred for these substituents.

The imidazo-pyrrolo-pyridines of the formula (II) and processes for their preparation are known (cf., for example, EP-OS (European Published Specification) 41,623).

Formula (III) provides a general definition of the substituted methane derivatives furthermore required as starting materials for carrying out the process according to the invention. In this formula (III), X, Y and Z preferably represent those radicals which have already been mentioned in connection with the description of the substances of the formula (I) according to the invention as being preferred for these substituents.

The substituted methane derivatives of the formula (III) are generally known compounds of organic chemistry.

Suitable diluents for carrying out the process according to the invention are inert organic solvents. These include, in particular, aliphatic, alicyclic or aromatic hydrocarbons, such as benzine, benzene, toluene, xylene, petroleum ether, hexane and cyclohexane, ethers, such as diethyl ether, dioxane, tetrahydrofuran or ethylene glycol dimethyl or diethyl ether, or alcohols, such as isopropanol or t-butanol.

The process according to the invention is carried out in the presence of a suitable basic reaction auxiliary. Suitable as such are all conventional inorganic or organic bases. Alkali metal alcoholates, such as, for example, sodium methylate or ethylate or potassium t-butylate, are used with particular advantage.

The reaction temperatures may be varied within a relatively wide range when carrying out the process according to the invention. In general, the process is carried out at temperatures between −20° C. and +60° C., preferably at temperatures between 0° C. and 30° C.

To carry out the process according to the invention, 1.0 to 1.5 moles, preferably equimolar amounts, of a substituted methane derivative of the formula (III) and 0.01 to 0.5 mole, preferably 0.1 to 0.2 mole, of a basic reaction auxiliary are generally employed per mole of an imidazo-pyrrolo-pyridine derivative of the formula (II). For work-up, the product is precipitated using a suitable organic solvent, dried and purified, if necessary, by reprecipitation or recrystallization.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyldeon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenochlea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, and for the selective combating of weeds in annual cultures.

The active compounds according to the invention can be employed here particularly successfully for pre- and post-emergence combating of weeds of mono- and dicotyledon weeds. At appropriate application rates, the active compounds according to the invention also have a growth-regulating action and can be used, for example, as cotton defoliants.

In addition, the substances according to the invention also have a good fungicidal and bactericidal action and can also be employed, at appropriately reduced application rates, for combating rice diseases, such as, for example, against the pathogen of rice spot disease (*Pyricularia oryzae*).

Depending on their respective physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol, as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons, as well as butane, propane, nitrogen and carbon dioxide.

As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules or organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumen hydrolyzation products; as dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is impossible to use colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beet, and 4-amino-6-(1,1-dimethylethyl)-3-methylthio-1,2,4-triazin-5(4H)-one for combating weeds in soya beans.

Mixtures with 2-chloro-4,6-bis-(ethylamino)-1,3,5-triazine, 5-amino-1,2,4-triazole, N-phosphonomethylglycine, N,N-dimethyl-N'-(3,4-dichlorophenyl)-urea, N,N'-dimethyl-N-(5-ethylsulphonyl-1,3,4-thiadiazol-2-yl)-urea, 2,4-dichlorophenoxyacetic acid, 2,4-dichlorophenoxypropionic acid, (2-methyl-4-chlorophenoxy)-acetic acid, (4-chloro-2-methylphenoxy)-propionic acid, 1,1'-dimethyl-4,4'-bipyridylium chloride, ammonium (3-amino-3-carboxypropyl)-methyl-phosphinate or methyl 2-{[(4,6-dimethyl-2-pyrimidinyl)-aminocarbonyl]-aminosulphonyl}-benzoate are also possible. Surprisingly, some mixtures also exhibit a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example, by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.05 and 10 kg of active compound per hectare of soil surface preferably between 0.1 and 5 kg per ha.

The preparation and use of the active compound according to the invention are evident from the examples which follow.

PREPARATION EXAMPLES

Example 1

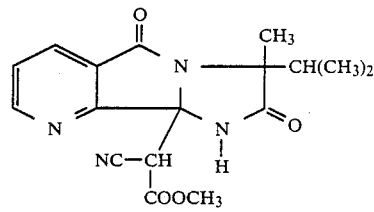

100 g (1 mol) of methyl cyanoacetate are added first, and 20 g (0.18 mol) of potassium t-butylate are added subsequently, to 243 g (1 mol) of 3-isopropyl-3-methyl-5H-imidazo-[1',2':1,2]pyrrolo[3,4-b]-pyridine-2-(3H),5-dione in 500 ml of toluene and 2,500 ml of t-butanol, the mixture is stirred for 6 hours at room temperature, 500 ml of toluene are added, and the mixture is stirred for a further 15 hours at room temperature. The resultant precipitate is filtered off under suction, washed with isopropanol/ether and dried.

273.1 g (80% of theory) of the compound of the formula given above, of the melting point 128° C.–131° C. (decomp.), are obtained.

The following imidazo-pyrrolo-pyridine derivatives of the general formula (I) are obtained in a corresponding fashion and according to the general instructions for the preparation:

TABLE 1

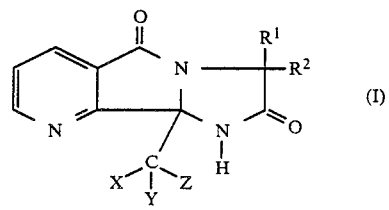

| Ex. No. | $R^1$ | $R^2$ | $-C{<}^X_{YZ}$ (i.e. $-C\genfrac{}{}{0pt}{}{X}{Y}Z$) | Melting point/°C. |
|---|---|---|---|---|
| 2 | CH$_3$ | (CH$_3$)$_2$CH— | $-C\genfrac{}{}{0pt}{}{Cl}{COOCH_3}{Cl}$ | 184 (decomp.) |
| 3 | CH$_3$ | (CH$_3$)$_2$CH— | $-CH\genfrac{}{}{0pt}{}{CO-CH_3}{COOCH_3}$ | 171 (decomp.) |

TABLE 1-continued

Structure (I):

Pyridine fused pyrrolinone with R¹, R² on carbon attached to N; CXYZ group on ring carbon with NH.

| Ex. No. | R¹ | R² | -C(X)(Y)(Z) | Melting point/°C. |
|---|---|---|---|---|
| 4 | CH₃ | (CH₃)₂CH— | —CH(COOCH₃)(COOCH₃) | 107 |
| 5 | CH₃ | C₂H₅ | —CH(COOCH₃)(COOCH₃) | 128–130 |
| 6 | —CH₂—CH₂—CH₂—CH₂—CH₂— | | —CH(COOCH₃)(COOCH₃) | 111 |
| 7 | CH₃ | C₂H₅ | —C(Cl)(Cl)(COOCH₃) | 184 |
| 8 | CH₃ | (CH₃)₂CH— | —C(Cl)(Cl)(COOC₂H₅) | 173 |
| 9 | CH₃ | (CH₃)₂CH— | —CH(COOC₂H₅)(CN) | 126 |
| 10 | CH₃ | (CH₃)₂CH— | —CH(Cl)(COOCH₃) | 143 |
| 11 | CH₃ | (CH₃)₂CH— | —CH₂—NO₂ | 132–134 |
| 12 | CH₃ | (CH₃)₂CH— | —CH₂—CO—CH₃ | 158 |
| 13 | CH₃ | (CH₃)₂CH— | —C(CH₃)(NO₂)(CH₃) | 143 |
| 14 | CH₃ | (CH₃)₂CH— | —CH(NO₂)(COC₂H₅) | 117 |
| 15 | CH₃ | (CH₃)₂CH— | —CH₂—CO—CH(CH₃)₂ | 146 |
| 16 | CH₃ | (CH₃)₂CH— | —CH₂—CO—(cyclopropyl) | 179 |
| 17 | CH₃ | (CH₃)₂CH— | —CH₂—CO—C₂H₅ | 164 |

USE EXAMPLES

In the following use examples, the compound shown below was employed as comparison substance:

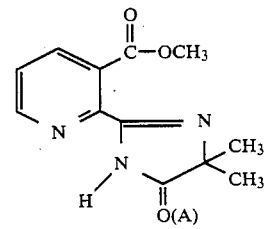

2-(4,4-dimethyl-5-oxo-2-imidazolin-2-yl)-3-methoxycarbonyl-pyridine.

(Disclosed by EP-OS (European Published Specification) 41,623)

Example A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the compounds according to Preparation Examples 1, 2, 3 and 4, for example, exhibit a clearly superior activity compared to comparison substance (A).

It will be appreciated that the instant specification and claims are set forth by way of illustration and not limitation, and that various modifications and changes may be made without departing from the spirit and scope of the present invention.

What is claimed is:

1. An imidazo-pyrrolo-pyridine compound according to formula

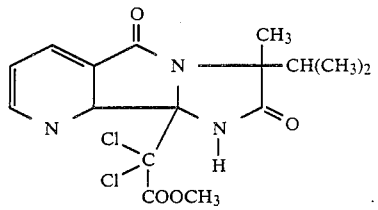

2. An imidazo-pyrrolo-pyridine compound according to formula

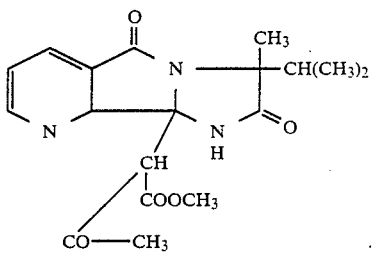

3. A herbicidal composition comprising a herbicidally effective amount of a compound according to claim 1, in admixture with an extender and/or a surface-active substance.

4. A herbicidal composition comprising a herbicidally effective amount of a compound according to claim 2, in admixture with an extender and/or a surface-active substance.

5. A method for combating unwanted vegetarian comprising applying to said vegetation or a locus from which it is desired to exclude said vegetation a herbicidally effective amount of a compound according to claim 1.

6. A method for combating unwanted vegetation comprising applying to said vegetation or a locus from which it is desired to exclude such vegetation a herbicidally effective amount of a compound according to claim 2.

* * * * *